United States Patent [19]

Lievense

[11] Patent Number: 5,045,465
[45] Date of Patent: Sep. 3, 1991

[54] FERMENTATION PROCESS FOR CREATININE IMINOHYDROLASE

[75] Inventor: Jefferson C. Lievense, Rochester, N.Y.

[73] Assignee: Eastman Kodak Company, Rochester, N.Y.

[21] Appl. No.: 393,184

[22] Filed: Aug. 14, 1989

[51] Int. Cl.$^5$ .............................................. C12N 9/78
[52] U.S. Cl. ................................ 435/227; 435/252.1; 435/253.1; 435/850
[58] Field of Search .................. 435/252.1, 227, 253.6, 435/850

[56] References Cited

U.S. PATENT DOCUMENTS

| 4,087,329 | 5/1978 | Terada et al. | 195/66 R |
| 4,134,793 | 1/1979 | Terada et al. | 195/103.5 R |
| 4,275,164 | 6/1981 | Masurekar | 435/227 |
| 4,276,377 | 6/1981 | Goodhue et al. | 435/18 |

OTHER PUBLICATIONS

Crueger, W. and Crueger, A., 1982, Biotechnology: A Textbook of Industrial Microbiology, Brock, D. (ed.) Science Tech, Inc.

J. Szulmajster, *J. Bacteriology*, "Bacterial Fermentation of Creatinine", vol. 75, pp. 633–639, (1958).

J. Szulmajster, *Biochimica et Biophysica Acta*, "Bacterial Degradation of Creatinine", vol. 30, pp. 154–163, (1958).

*Primary Examiner*—Lester L. Lee
*Assistant Examiner*—E. J. Kraus
*Attorney, Agent, or Firm*—Doreen M. Wells

[57] ABSTRACT

A fermentation process and improved aqueous nutrient medium are used for the production of urease-free creatinine iminohydrolase from an aerobic soil microorganism. In the process, an inoculum culture of the microorganism is transferred into a production medium to generate microorganisms in which creatinine iminohydrolase production has been induced, said nutrient medium containing a source of ammonia and after the ammonia is substantially exhausted, incrementally adding a solution of creatinine, controlling the pH by addition of α-ketoglutaric acid, and extracting urease-free creatinine iminohydrolase. An improved aqueous nutrient medium for use as the production medium is disclosed.

18 Claims, No Drawings

FERMENTATION PROCESS FOR CREATININE IMINOHYDROLASE

FIELD OF THE INVENTION

The present invention relates to a process and an improved aqueous nutrient medium for growing an aerobic soil microorganism which produces urease-free creatinine iminohydrolase.

BACKGROUND OF THE INVENTION

Creatinine iminohydrolase is an enzyme which specifically hydrolyzes creatinine to ammonia. Accordingly, by contacting an aqueous liquid containing creatinine with this enzyme to generate ammonia, the presence and/or concentration of creatinine in the liquid can be determined by detecting the level of generated ammonia. This enzyme can therefore play an important role in the clinical laboratory where it can be used as a diagnostic test reagent for the determination of creatinine in biological liquids.

Creatinine iminohydrolase, sometimes referred to as creatinine desimidase, has been obtained from various microorganisms. For example, J. Szulmajster in *J. Bacteriolol*, 75: 633 (1958) and *Biochim Biophys Acta*, 30: 154 (1958) describes a preparation of creatinine iminohydrolase obtained from the anaerobic, gram-positive microorganism *Clostridium parapurtrificum*. A method of growing the *Clostridium parapurtrificum* microorganism is also described in these Szulmajster publications. However, these publications relate specifically to an anaerobic, gram-positive microorganism, and the disclosed fermentation method for growing the microorganism requires a long time. Moreover, the amount of microbial cells grown and the yield of enzyme extracted therefrom is relatively small.

U.S. Pat. Nos. 4,087,329 and 4,134,793 describe the production of the enzyme creatinine desimidase from one of several aerobic microbial sources including microorganisms of the genera Brevibacterium, Corynebacterium, Pseudomonas, and Arthrobacter. These patents further describe a nutrient medium which may be used for culturing microorganism of the aforementioned genera. These patents assert that the formulation of this nutrient medium can be widely varied and can contain any of a large number of specifically recited carbon and nitrogen sources, as well as other optional nutrients, including inorganic materials, a creatinine inducer, and the like.

Goodhue, Esders, and Masurekar U.S. Pat. No. 4,276,377 describes and claims a creatinine iminohydrolase enzyme preparation free from urease activity obtained from an aerobic soil microorganism, preferably the aerobic soil microorganism ATCC 31546. Because this enzyme preparation is free of urease contamination and is highly specific for creatinine, creatinine assays can be performed with this enzyme without regard to interference by urea and other nitrogenous substances that are often present in biological aqueous liquids to be assayed for creatinine, e.g., serum. The urease-free creatinine iminohydrolase enzyme preparation described therein is therefore highly desirable.

Masurekar's U.S. Pat. No. 4,275,164 describes a process for the production of creatinine iminohydrolase from an aerobic soil microorganism by transferring a growth microorganism to a production medium having a pH in the range 5 to 10 and extracting urease-free creatinine iminohydrolase. The production medium comprises a carbon source containing glucose or an amino acid precursor, a nitrogen source containing creatinine, trace nutrients and a buffer. Although the process produces excellent enzyme activity (as units per liter) and high specific activity (as units per gram dry cell mass), further improvement is susceptible to the toxic effects of fermentation medium components at high concentration and metabolites such as N-methylhydantoin which decrease productivity and yield. In addition, the use of complex nutrient sources such as yeast extract makes the fermentation susceptible to contamination by foreign microbes which decrease the fermentation productivity and enzyme activity, as well as themselves being a source of impurities that make subsequent enzyme recovery and purification more difficult.

An improved process from that described in U.S. Pat. No. 4,275,164 for providing a creatinine iminohydrolase with increased yield would represent a clearly advantageous addition to the art. Such a process and nutrient medium used therein would be particularly desirable if useful with the aerobic soil microorganism ATCC 31546.

SUMMARY OF THE INVENTION

The present invention provides an improved fermentation process and improved aqueous nutrient medium for growing under aerobic conditions an aerobic soil microorganism from which a creatinine iminohydrolase enzyme preparation can be obtained.

In one embodiment, the invention provides a fermentation process for production of creatinine iminohydrolase from an aerobic soil microorganism maintained on an aqueous maintenance medium containing creatinine under aerobic conditions. The fermentation process comprises the steps of 1) transferring a seed culture of the microorganism to a production medium having a pH in the range of about 7 to 8 to generate, under aerobic conditions, a high concentration of the microorganism wherein the aqueous nutrient medium comprises:
   a) a carbon source comprising α-ketoglutaric acid and glucose,
   b) a nitrogen source comprising a source of ammonia, and
   c) salts which are sources of inorganic nutrients, and
2) incrementally adding, when ammonia is substantially exhausted, a solution of creatinine at a rate of about 0.5 to 3 grams per liter of fermentation broth per hour to induce synthesis of creatinine iminohydrolase to a high level, and
3) controlling the fermentation pH to about 7 to 8 by addition of an aqueous solution containing α-ketoglutaric acid, glucose, and inorganic salts, and
4) extracting urease-free creatinine iminohydrolase from said medium.

In a preferred embodiment, the improved fermentation process and improved aqueous nutrient medium of the invention have been found useful for production of urease-free creatinine iminohydrolase from an aerobic soil microorganism such as ATCC 31546. The term "urease-free" as defined herein refers to an enzyme preparation that in crude, unpurified form as extracted and separated from the microbial cells in which it was produced exhibits substantially no urease activity. A typical assay procedure for determining urease activity can be carried out using the method of Procedure 4 hereinafter.

DESCRIPTION OF THE PREFERRED EMBODIMENTS

The process of the present invention provides an improved aqueous nutrient medium for the growth of an aerobic soil microorganism, preferably the microorganism ATCC 31546, from which increased yields of creatinine iminohydrolase can be obtained. The microorganism identified as ATCC 31546 has received this designation based on its deposit with the American Type Culture Collection, Rockville, Md. 20852 U.S.A. on July 26, 1979. The written description of ATCC 31546 which appears in commonly-owned U.S. Pat. No. 4,276,377 at column 3, lines 16–64, is hereby incorporated by reference. This microorganism has been tentatively assigned to the genus Flavobacterium and given the species name filamentosum.

The fermentation process described hereinabove facilitates good growth of the microorganism and significantly improves yield of the enzyme. Unexpectedly, these highly advantageous results are achieved in the process by growing a seed culture of the microorganism and inducing enzyme production by a two phase process of 1) transferring the seed culture of the microorganism to a production medium having a pH in the range of about 7 to 8 to generate, under aerobic conditions, a high concentration of the microorganism, said production medium representing an aqueous nutrient medium which comprises:
   a) a carbon source comprising α-ketoglutaric acid and glucose,
   b) a nitrogen source comprising a source of ammonia, and
   c) salts which are sources of inorganic nutrients, and
2) after the first phase and when ammonia is substantially exhausted, incrementally adding a solution of creatinine at a rate of about 0.5 to 3 grams of creatinine per liter of fermentation broth per hour to induce synthesis of creatinine iminohydrolase to a high level. The pH is controlled throughout the fermentation at about 7 to 8 by addition of an aqueous solution containing α-ketoglutaric acid, glucose and inorganic salts. High yields of creatinine iminohydrolase in excess of 11,400 units per liter of fermentation broth in 27.4 hours and a specific enzyme activity of 460 units per gram dry cell mass are obtained.

Seed Medium

The microorganism can be grown in any conventional medium such as that described in U.S. Pat. No. 4,275,164. Thus, a fresh sample of aerobic soil microorganism can be inoculated into a seed medium having a pH of from about 5 to about 10 to grow the microorganism. The seed medium can comprise nutrients including carbon sources such as glucose and α-ketoglutaric acid, nitrogen sources such as glutamic acid, creatinine, and ammonium salts, and inorganic salts which buffer the medium and supply trace inorganic nutrients. Other complex nutrients from natural sources such as vegetable or nonpeptic milk protein hydrolysates may be incorporated to supplement or replace the other medium components as described in U.S. Pat. No. 4,275,164.

Production Medium

The production medium useful herein comprises a carbon source, nitrogen source and inorganic salts.

The carbon source is a mixture of α-ketoglutaric acid and glucose. The carbon source could also include other sources of carbon such as citric acid, fumaric acid, malic acid, lactic acid, and the like in place of or together with α-ketoglutaric acid and glucose.

The amount of α-ketoglutaric acid in the initial medium can vary. Useful amounts have been found to be in the range of about 20 to 80 grams per liter, preferably about 20 to 30 grams per liter. The starting medium preferably contains about 30 to 100 grams per liter of total carbon source.

The nitrogen source employed in the initial production medium comprises a source of ammonia such as ammonium sulfate, ammonium hydroxide, glutamic acid, and the like. The preferred nitrogen source is ammonium sulfate.

The amount of ammonium sulfate in the initial medium can vary. Useful amounts have been found to be in the range of about 5 to 20 grams per liter, preferably about 10 to 15 grams per liter.

Inorganic salts are employed in the production medium to satisfy inorganic nutrient requirements of the microorganism. Typically these trace inorganic salts are added in small quantities. Yeast extract and vitamins can also be present as optional sources of trace nutrients.

Typical inorganic salts which can be present as trace nutrients include salts of phosphorus, sulfur, chlorine, potassium, sodium, magnesium, calcium, iron, zinc, manganese, molybdenum, and other salts. One inorganic salt mixture which has been found especially useful is an aqueous 0.1N HCl solution of the following composition, the concentration of each listed component based on the amount present in one liter of aqueous solution:

| | |
|---|---|
| $MgSO_4.7H_2O$ | 12.2 g |
| $CuCl_2.2H_2O$ | 0.076 g |
| $FeSO_4.7H_2O$ | 2.8 g |
| $MnSO_4.H_2O$ | 1.7 g |
| $ZnSO_4.7H_2O$ | 0.06 g |
| $NaCl$ | 0.6 g |
| $NaMoO_4.2H_2O$ | 0.1 g |

The aqueous nutrient medium representing the production medium can also contain other salts, such as a phosphorous-containing salt, as well as salts also included in the salt mixture. A preferred phosphate salt is dipotassium hydrogen phosphate, $K_2HPO_4$, typically present in an amount within the range of about 5 to 15 grams per liter, preferably about 10 to 12 grams per liter.

The pH of the aqueous nutrient medium representing the production medium is typically in a range of from about 7.0 to 8.0. The pH of the initial medium can readily be adjusted to a value in the aforementioned range by addition of a base such as KOH or NaOH, preferably NaOH.

The production medium can also contain other optional components as will be appreciated by those skilled in the art. Because foaming is often encountered when growing microorganisms in a large-scale fermentation, foam control agents can be included in the medium. One such foam control agent which can be employed is a polyglycol such as Polyglycol P-2000, a tradename of Dow Chemical Company, Midland, Mich. Typically, when used, this foam control agent is employed in an amount up to about 0.5 gram per liter although lower amounts of 0.1 gram per liter have generally been found sufficient to control foaming. Other foam control agents can also be used; the main criterion for selection being minimal or no inhibition of microbial growth and enzyme synthesis at a concentration level that will control the foam.

Fermentation Process For Enzyme Production

The above-described production medium is advantageously employed in the first phase of the final step of a fermentation process suitable for large-scale production of creatinine iminohydrolase from an aerobic soil microorganism such as the microorganism ATCC 31546.

This fermentation process employs a sample of the microorganism grown on a maintenance medium under aerobic conditions at pH conditions similar to those described above for the production medium. Thus, the pH is typically adjusted from about 5.0 to 10.0, preferably about 7.0 to 8.0 by addition of base, preferably NaOH or KOH, although other bases may also be employed. The temperature of the maintenance medium is typically within the range of from about 15° to 42° C., preferably about 25° to 30° C.

The maintenance medium typically comprises an aqueous medium including a carbon source preferably including one or more of the above-described amino acid precursors representing an organic acid free from amino groups together with glucose; a nitrogen source comprising creatinine; trace nutrients such as one or more inorganic salts and optionally yeast extract and vitamins; buffer; and agar.

A maintenance medium which has been found especially useful has the following composition, the concentration of each listed component based on the amount present in one liter of the maintenance medium:

| | |
|---|---|
| Agar | 20.0 g |
| Fumaric acid (carbon source) | 10.0 g |
| Creatinine (nitrogen source) | 5.0 g |
| K$_2$HPO$_4$ as buffer (anhydrous) | 5.0 g |
| Salt solution | 10.0 ml |
| Distilled water | 800.0 ml |
| pH adjusted to 7.0 with KOH and volume made up to 1 liter with distilled water. | |

The salt solution noted immediately hereinabove is a 0.1N HCl aqueous solution and has the following composition, the concentration of each listed component based on the amount present in one liter of salt solution:

| | |
|---|---|
| MgSO$_4$.7H$_2$O | 12.2 g |
| CaCl$_2$.2H$_2$O | 0.076 g |
| FeSO$_4$.7H$_2$O | 2.8 g |
| MnSO$_4$.H$_2$O | 1.7 g |
| ZnSO$_4$.7H$_2$O | 0.06 g |
| NaCl | 0.6 g |
| NaMoO$_4$.2H$_2$O | 0.1 g |

The fermentation process is initiated wherein a "fresh" sample of the microorganism is transferred to a microbial seed medium to grow the microorganism. The term "fresh" sample of microorganism refers to a sample of the microorganism which has been incubated and maintained in the maintenance medium at about 25° C. for a relatively short duration, typically on the order of from about 24 to 72 hours, preferably about 48 hours.

To provide a ready supply of fresh sample of microorganism obtained from the maintenance medium, one can store the microorganism as a freeze-dried powder at temperatures in the range of from about 4° to 25° C., thereby suspending cellular growth processes of the microorganism. New cultures of the freeze-dried powder in the above-described maintenance medium can then be periodically initiated as desired. In this way, one can provide a continual supply of "fresh" sample of the microorganism for transfer to the microbial growth medium of the fermentation.

Alternatively, one can also provide a supply of fresh sample of microorganism by storing it frozen in liquid nitrogen as described in the appended Procedures.

The composition of the microbial seed medium in preparing the growing microorganism of the fermentation process, although important, can vary widely. In general, the microbial seed medium is selected to achieve maximal cell growth of the microorganism consistent with good yields of enzyme production in the process. A medium of the following composition is preferred:

| | |
|---|---|
| Na$_2$α-KG (Disodium α-ketoglutarate) | 12.5 g/l |
| Creatinine | 6.7 g/l |
| Glucose | 5.0 g/l |
| MgSO$_4$.7H$_2$O | 0.8 g/l |
| KH$_2$PO$_4$ | 5.0 g/l |
| Salt Solution | 8.3 ml/l |

The temperature conditions for the microorganism in the seed medium can vary. Typically, good cell growth in the seed medium in the process occurs over a temperature range of from about 20° to 37° C., preferably about 25° to 30° C.

The sample of microorganism which is transferred to the microbial seed medium is incubated in this seed medium for a period effective to obtain good cell growth of the microorganism. The effective time period of this can vary depending upon the composition of the medium as well as the number of cells transferred to the growth medium. In case of a preferred microbial seed medium, the effective incubation period for a sample of the microorganism obtained from the maintenance medium and inoculated into a flask containing 25 ml of the microbial seed medium is about 24 hours.

Having grown the microorganism, the microbial seed medium containing the growing cells is transferred to the production medium. The microbial seed medium containing growing cells is typically transferred, in total, to the production medium. This microbial seed culture (i.e., the microbial seed medium and the growing cells contained therein) thus serves as an inoculum for the production medium.

The production medium is contained in a fermentor. Such a fermentor has a capacity of at least 10 liters, typically 150 liters to 200,000 liters. Depending upon the size of the final production fermentor, the preparation of the microbial seed medium containing the growing cells can be carried out in stages to obtain a sufficient quantity of microbial seed culture to serve as the inoculum for the final production fermentor.

For instance, in the case where the final production fermentor has a volume of approximately 150 liters, the growth is advantageously carried out in two stages.

Typically, in each stage of the growth step the cell growth of the microorganism in the microbial seed medium is maximized and the resultant culture (containing both the medium and growing cells) is used as an inoculum for a succeeding stage in which the culture is introduced into a new, generally larger batch of microbial seed medium.

The composition of the production medium employed in the present fermentation process is as described in the "Production Medium" section of this specification. Likewise, the pH conditions maintained during incubation of the microorganism in the production medium are identical to those described in the "Production Medium" section. Sufficient oxygen to maintain maximum enzyme production by the microorganism is also important. This can readily be determined by monitoring the dissolved oxygen concentration in the production medium. The air flow rate and the agitation rate of the medium are varied to prevent oxygen limitation. The incubation time for the microorganism in phase one of the fermentation process will vary depending on the specific composition of the production medium, the oxygen transport rate, temperature, and other conditions. Typical incubation times for a 14-liter production scale fermentor are within the range of from about 10 to 14 hours. As described above, if necessary or desirable, anti-foam agents can be added at an earlier stage of the fermentation multi-stage process to the microbial seed medium.

An aerobic soil microorganism such as ATCC 31546 grown in the production medium of the present fermentation process can generally be grown over a reasonable range of temperatures to produce good yields of creatinine iminohydrolase enzyme. Good results can be obtained in a temperature range of from about 20° to 37° C. Best results have typically been achieved at a temperature of about 25° to 30° C.

The fermentation process for production of creatinine iminohydrolase from the grown microorganism is carried out in two phases. In the first phase, the seed culture containing the microorganism is transferred to the production medium described above. The source of ammonia is supplied in excess to support rapid growth and only a small amount of creatinine iminohydrolase is actually produced. The end of the first phase corresponds with the exhaustion of ammonia and is marked by a sharp drop in the gas exchange rates as determined by a sudden decrease in the rates of oxygen consumption and $CO_2$ production and a sudden increase in the dissolved oxygen concentration at fixed agitation and air flow rates. The second phase is initiated immediately upon observation of these changes.

In the second phase of the production fermentation, a solution of creatinine is added incrementally by feeding at a fixed growth-limiting rate of from about 0.5 to 3 grams creatinine per liter per hour. The resulting nitrogen-limited condition in the presence of creatinine, the inducer of creatinine iminohydrolase, causes a high rate of enzyme synthesis. The preferred rate of addition of creatinine is from 1 to 1.5 grams creatinine per liter per hour.

During both phases, the pH is controlled at 7 to 8 by the addition of a solution containing α-ketoglutaric acid. We have found that in an uncontrolled fermentation, the pH tends to increase due to the depletion of the organic acid carbon source. Using the α-ketoglutaric acid addition controls the pH effectively and causes α-ketoglutaric acid to be replaced as it is consumed.

Thus this method of pH control also allows lower starting concentrations of nutrients such as α-ketoglutaric acid, glucose, and salts which at high concentrations inhibit the growth of the microorganism and production of creatininase iminohydrolase.

The solution of α-ketoglutaric acid advantageously contains at least 300 grams per liter of α-ketoglutaric acid. The solution can comprise other materials as well, such as glucose and trace elements, such as $Mg^{2+}$, $Mn^{2+}$, $Fe^{2+}$ and $Zn^{2+}$ to insure that adequate amounts of these components are supplied at noninhibitory concentrations. Generally, the solution comprises from

| 80 to 120 g/l | Glucose |
| 5 to 10 g/l | $MgSO_4.7H_2O$ |
| 0.1 to 1 g/l | $FeSO_4.7H_2O$ |
| 0.1 to 1 g/l | $MnSO_4SO_4.H_2O$ |
| 0.01 to 0.1 g/l | $ZnSO_4.7H_2O$. |

The rate of addition of α-ketoglutaric acid solution will vary according to the pH of the medium. The pH is monitored by a pH electrode, and additional solution is added automatically when the pH exceeds the desired value. Thus, the rate of addition is typically less than 1 ml per liter per hour at the beginning of the first phase and increases to 15 ml per liter per hour or more by the end of the second phase.

The second phase of the production fermentation can generally run from 10 to 15 hours. The length of time for this phase is determined by measurement of the creatinine iminohydrolase activity. When the activity level reaches a maximum, the fermentation is stopped.

Following completion of the second phase, the desired urease-free creatinine iminohydrolase enzyme is recovered from the microbial cells in step 3. This can be accomplished by conventional means whereby the cells are disrupted by sonication, grinding, or the like; and the desired enzyme preparation is separated from the medium by organic solvent fractional precipitation or other conventional enzyme separation and purification techniques. An especially preferred method for recovering the desired enzyme and to obtain increased enzyme yield is described in McCollough, Esders and Lynn, U.S. Pat. No. 4,275,166.

The following nonlimiting example is provided to further illustrate the invention. In the example, the following materials were used:

| 1. | Microorganism - the aerobic soil microorganism ATCC 31546 | |
|---|---|---|
| 2. | Medium No. 1 (microbial maintenance medium) | |
| | Agar | 20.0 g/l |
| | Fumaric acid (carbon source) | 10.0 g/l |
| | Creatinine (nitrogen source) | 5.0 g/l |
| | $K_2HPO_4$ (anhydrous) | 5.0 g/l |
| | Modified Salt Solution C | 10.0 ml |
| | Distilled Water | 800.0 ml |
| | pH was adjusted to 6.7 with KOH, and made up to 1 liter with distilled water. | |
| | Composition of Modified Salt Solution C: | |
| | $MgSO_4.7H_2O$ | 12.2 g/l |
| | $CaCl_2.2H_2O$ | 0.076 g/l |
| | $FeSO_2.7H_2O$ | 2.8 g/l |
| | $MnSO_4.H_2O$ | 1.7 g/l |
| | $ZnSO_4.7H_2O$ | 0.06 g/l |
| | NaCl | 0.6 g/l |
| | $NaMoO_4.2H_2O$ | 0.1 g/l |
| | Made up to 1 liter with 0.1 N HCl | |
| 3. | Medium No. 2 (seed medium) | |
| | Glucose | 5.0 g/l |

-continued

| | | |
|---|---|---|
| $Na_2$α-ketoglutarate | 12.5 | g/l |
| Creatinine | 6.7 | g/l |
| $K_2HPO_4$ | 5.0 | g/l |
| $MgSO_4.7H_2O$ | 0.8 | g/l |
| Modified Salt Solution C | 8.3 | ml/l |
| Initial pH 8.3 (requires no adjustment) | | |
| 4. Medium No. 3 (initial medium for production) | | |
| α-Ketoglutaric acid | 18.2 | g/l |
| $Na_2$α-ketoglutaric acid | 5.5 | g/l |
| Glucose | 10.6 | g/l |
| $(NH_4)_2SO_4$ | 10.9 | g/l |
| Creatinine | 0.45 | g/l |
| $K_2HPO_4$ | 10.0 | g/l |
| $MgSO_4.7H_2O$ | 1.5 | g/l |
| KOH (brings medium to pH 7.05) | 17.0 | g/l |
| Modified Salt Solution C | 15.0 | ml |
| Polyglycol (2000) | 0.15 | ml |
| The creatinine feed solution contains: | | |
| Creatinine | 74 | g/l |
| The α-ketoglutaric acid feed solution contains: | | |
| α-Ketoglutaric acid | 373.0 | g/l |
| Glucose | 110.0 | g/l |
| $MgSO_4.7H_2O$ | 6.7 | g/l |
| $MnSO_4.H_2O$ | 0.2 | g/l |
| $FeSO_4.7H_2O$ | 0.4 | g/l |
| $ZnSO_4.7H_2O$ | 0.01 | g/l |

In the example, the following procedures were used:

Procedures

1. Culture Preservation and Maintenance

A culture of the microorganism ATCC 31546 was preserved by growing the culture for ten hours at 30° C. in Tryp-Soy Broth, a "complex" medium composed of a vegetable protein hydrolysate sold by Scott Laboratories Inc. Fiskeville, R.I. The cells were then separated aseptically and resuspended in sterile 10% aqueous glycerol with Allen's salt solution (Allen, M. B., Archives of Microbiology, Vol. 32, p. 270-277 (1959). A small volume, 0.5-2.0 ml of this culture was added to a sterile glass ampoule which was then sealed and stored in liquid nitrogen. To obtain a sample of the microorganism, the culture in the ampoule was thawed and the contents were aseptically transferred to Tryp-Soy Broth and grown for 10 hours at 30° C. A loopfull of this culture was transferred aseptically to slants of Medium No. 1 incubated at 25° C.

2. Enzyme Production

Enzyme production was achieved in a 14-liter fermentor as follows:

First, a fresh sample of the microorganism ATCC 31546 culture grown for two days on Medium No. 1 slants as described in Procedure 1 above was obtained. From this slant, a loopfull of culture was inoculated into 25 ml of a microbial seed medium contained in each of four 250-ml Erlenmeyer flasks. The microbial seed medium employed consisted of Medium No. 2, referred to hereinabove. Following inoculation of the culture into the four Erlenmeyer flasks, the flasks were shaken at 200 rpm at 25° C. for 24 hours to produce good cellular growth. Then the contents of the four flasks were transferred equally to two Fernbach flasks each containing 450 ml of Medium No. 2. The Fernbach flasks were shaken at 100 rpm at 25° C. for 16 hours.

The first phase of the production fermentation was carried out by transferring the contents of the two Fernbach flasks into a 14-liter fermentor containing 6.6 liters of an initial production medium. The production medium employed consisted of Medium No. 3, referred to hereinabove.

The temperature was maintained at 25° C. The dissolved oxygen concentration was maintained at or above 20 percent of the air saturation concentration by agitation and aeration of the medium. The pH was controlled at 7.3 to 7.8 by automatic addition of the α-ketoglutaric acid feed solution described hereinabove as a part of Medium No. 3.

The rates of oxygen consumption and carbon dioxide production were monitored with the aid of a mass spectrometer which provided measurements of the inlet and exhaust gas compositions. The rates were calculated by a material balance on the gas streams. Samples of the fermentation broth were taken periodically for off-line analysis of the cell dry weight concentration. In addition, 2.5 ml aliquots of the culture samples were centrifuged at 5000 rpm in a refrigerated centrifuge to separate the cells from the production medium. The supernatants containing the production medium were saved for later analysis of chemical component concentrations. The cells were disrupted and assayed for creatinine iminohydrolase activity as described in Procedures 4 and 5.

Upon exhaustion of the ammonium supplied in the initial medium, the rates of oxygen consumption and carbon dioxide production were observed to decrease noticeably and suddenly. The dissolved oxygen concentration similarly increased. This marked the end of the first phase of production.

The second phase of the production fermentation was carried out by initiating the addition of creatinine to the fermentor at a fixed rate of 181 ml per hour immediately upon observing the changes in rates and dissolved oxygen noted above. The feed solution employed is described hereinabove as part of Medium No. 3. All other conditions were as described for the first phase.

Due to the greatly increased microorganism concentration and rate of metabolism of carbon source, the rate of automatic addition of the α-ketoglutaric acid feed solution was much faster than at the beginning of the first phase of the production fermentation. The fermentation was halted after 27.4 hours of operation after the rate of increase in the creatinine iminohydrolase activity had slowed.

3. Cell Disruption: Sonication

A sample of well agitated fermentation mixture (5.0 ml) is centrifuged for five minutes at 17,000 rpm in a centrifuge tube, the supernate decanted and discarded, and the pellet resuspended in 4.9 ml of 0.1M tris phosphate buffer. The tris phosphate buffer is prepared by dissolving 12.1 grams of Sigma Chem. Co. T-1503 Trizma base in 800 ml of deionized water, adjusting the pH at 25° C. to 7.5 with phosphoric acid and diluting with deionized water to a final volume of 1000 ml.

Another 5.0 ml of 0.1M tris phosphate buffer is added and the sample is transferred to a Rosette cell for sonication. The Rosette cell is placed in an ice bath and sonicated at an output setting of 2 for five minutes using an Ultrasonic Inc. W-375A Sonifier having a 3/16 inch (9.5 mm) tapered microtip disrupter horn. The horn is placed carefully into the mixture to avoid touching the cell walls. A 5.0 ml sample of the sonicated material is transferred by pipette to a 10 ml volumetric flask and diluted to 10 ml with the 0.1M tris phosphate buffer. The total dilution factor from the original sample is 4X.

4. Assay of Creatinine Iminohydrolase

Creatininase converts creatinine to N-methylhydantoin and ammonia, thus it can be assayed by monitoring the rate of disappearance of NADPH ($\beta$-nicotinamide adenine dinucleotide phosphate-reduced) during a second stage reaction in which $\alpha$-ketoglutaric acid and ammonia are converted to glutamic acid in the presence of glutamate dehydrogenase.

$$\alpha\text{-Ketoglutarate} + NH_4^+ + NADPH \rightleftharpoons \text{glutamate} + NADP^+ + H_2O$$

The following stock solutions were prepared:

A. 0.1M Bicine Solution

Sigma B-3876 Bicine (16.3 g) is dissolved in 800 ml of deionized water, the pH adjusted to 7.6 with 1N KOH at 25° C., and the solution diluted to 1000 ml with distilled water (store refrigerated).

B. $\alpha$-Ketoglutaric Acid/EDTA Solution

Ethylenediaminetetracetic acid (EDTA) (0.4 g) and $\alpha$-ketoglutaric acid (1.6 g) are dissolved in 80 ml of deionized water, the pH adjusted to 7.5 at 25° C. with 50 percent NaOH solution, and the mixture diluted to 100 ml with deionized water (store frozen).

C. 0.4M Creatinine Solution

Sigma C-4255 creatinine (0.45 g) is dissolved in 10 ml of deionized water and stored frozen.

D. 0.01M NADPH Solution

Sigma N-1630 NADPH (0.080 g) is dissolved in 10 ml of deionized water and stored frozen.

E. Stock Reaction Mixture

The above stock solutions were used to prepare a stock reaction mixture having the following composition:

| | |
|---|---|
| 0.1 M Bicine Solution A | 7.4 ml |
| $\alpha$-Ketoglutaric Acid/EDTA Solution B | 1.0 ml |
| 0.4 M Creatinine Solution C | 1.0 ml |
| Sigma G-2626 L-Glutamic Dehydrogenase | 300 U |
| 0.01 M NADPH Solution D | 0.3 ml |

The fermentation samples were analyzed in a Caoz 219 Spectrophotometer by adding 10 ml of diluted sample prepared as in 3 above [Cell Disruption (Analytical Sample Preparation)] to 0.99 ml of the Stock Reaction Mixture E in a cuvette, covering the cuvette with parafilm, and placing in the sample compartment of the spectrophotometer. The decrease in NADPH is monitored by following the absorbence at 340 nm for 10 minutes and the calculated activity of the creatininase iminohydrolase is reported.

EXAMPLE 1

Results of Creatinine Iminohydrolase Production Using a Two-Phase Fermentation This example reports the increase in yield and productivity of creatinine iminohydrolase enzyme obtained from aerobic soil microorganisms grown by a two-phase fermentation process using an improved aqueous nutrient medium. The urease-free creatinine iminohydrolase-producing microorganism ATCC 31546 described in Procedure 1 above was grown according to Procedure 2, also described above. The microbial cell pellets obtained as described in Procedure 2 were disrupted as in Procedure 3 and were assayed as described in Procedure 4 to determine their creatinine iminohydrolase activity and thus obtain a quantitative evaluation of the yield of creatinine iminohydrolase and the fermentation productivity. The results are set out below in Table I. The elapsed fermentation time was measured from the moment that the contents of the two Ferbach seed flasks were added to the production medium.

The first phase of the fermentation extended from time 0 through 12.1 hours. During this time interval, the cell mass concentration increased rapidly to 16 grams dry mass per liter and the oxygen consumption rate similarly increased to over 150 mmole per liter per hour, but relatively little increase in creatinine iminohydrolase was observed. The oxygen consumption rate was observed to decrease suddenly at 12 hours. This was taken to indicate that ammonia in the medium was exhausted, as confirmed by analysis of the ammonia concentration. Consequently, the feeding of the creatinine solution at a fixed rate of 181 ml per hour was begun at 12.1 hours. This marked the beginning of the second phase.

Shortly after the creatinine feed was begun, the creatinine iminohydrolase activity began to increase rapidly, indicative of the induction of its synthesis by creatinine. The increases in cell mass concentration and oxygen consumption rate in the second phase are indicative of the limiting effects of the creatinine feed on cell mass production and carbon source metabolism.

The $\alpha$-ketoglutaric acid solution, containing also glucose and inorganic salts, was fed automatically throughout the fermentation to control the medium pH between 7 and 8. In this way carbon limitation of the fermentation was automatically avoided without any danger of the carbon source concentration becoming too high and inhibiting cell mass and creatinine iminohydrolase production. Between 23 and 24 hours, however, it was necessary to add a small volume of aqueous solution containing 50 grams of $\alpha$-ketoglutaric acid that had been neutralized with KOH. This action was taken because a drop in the oxygen consumption rate was observed during this time interval, indicating a carbon source limitation despite the continuous addition of carbon to control the medium pH. It is evident, in a variation of this procedure, that the concentration of $\alpha$-ketoglutaric acid in the initial production medium could be increased by about 10 grams per liter to avoid the occurrence of a carbon source limitation during the second phase.

The fermentation was stopped at 27.43 hours when the rate of increase in creatinine iminohydrolase activity had slowed. At this point, the activity was over 11,400 units per liter and the specific activity was 460 units per gram dry cell mass. This represents a large and significant improvement over the results obtained using the method described in U.S. Pat. No. 4,275,164.

TABLE I

| Elapsed Fermentation Time (Hours) | Ammonia Concentration (g/l) | Cell Mass Concentration (g dry mass/L) | Creatinine Iminohydrolase (units/l) | Specific Creatinine Iminohydrolase activity (units/g dry mass) | Oxygen Consumption rate (mmole/l/hour) | Total Volume α-ketoglutaric Acid Fed (liters) |
|---|---|---|---|---|---|---|
| 0.0 | 2.0 | 0.51 | 69 | 135 | 3.8 | 0.012 |
| 1.0 | 1.8 | 0.55 | 48 | 87 | 4.7 | 0.029 |
| 2.0 | 2.3 | 0.66 | 66 | 100 | 6.6 | 0.032 |
| 3.0 | 2.3 | 0.90 | 80 | 89 | 8.0 | 0.035 |
| 4.0 | 2.2 | 1.0 | 72 | 71 | 15. | 0.048 |
| 5.0 | 1.6 | 1.5 | 71 | 46 | 16. | 0.054 |
| 6.0 | 2.3 | 2.2 | 125 | 58 | 16. | 0.072 |
| 7.0 | 1.8 | 2.9 | 123 | 43 | 32. | 0.091 |
| 8.0 | 1.6 | 4.1 | 108 | 26 | 46. | 0.121 |
| 9.0 | 1.8 | 5.6 | 132 | 24 | 65. | 0.169 |
| 10.1 | 0.7 | 8.2 | 141 | 17 | 97. | 0.239 |
| 11.1 | 0.4 | 13. | 221 | 17 | 140 | 0.332 |
| 12.1 | 0.0 | 16. | 268 | 17 | 98 | 0.480 |
| 13.0 | 0.0 | 17. | 538 | 33 | 117. | 0.539 |
| 14.0 | 0.0 | 18. | 1600 | 91 | 150 | 0.649 |
| 15.0 | 0.0 | 18. | 3020 | 168 | 150 | 0.788 |
| 16.1 | 0.0 | 19. | 4030 | 214 | 150 | 0.928 |
| 17.0 | 0.0 | 20. | 4560 | 226 | 150 | 1.04 |
| 18.1 | 0.0 | 21. | 5080 | 243 | 160 | 1.16 |
| 19.1 | 0.0 | 21. | 6590 | 309 | 160 | 1.29 |
| 20.1 | 0.0 | 22. | 7140 | 328 | 160 | 1.43 |
| 21.1 | 0.0 | 23. | 8380 | 371 | 160 | 1.58 |
| 22.2 | 0.0 | 23. | 8360 | 364 | 160 | 1.73 |
| 23.2 | 0.0 | 24. | 9000 | 381 | 150 | 1.89 |
| 24.3 | 0.0 | 24. | 9560 | 406 | 130 | 2.04 |
| 25.2 | 0.0 | 24. | 8960 | 368 | 150 | 2.41 |
| 26.4 | 0.0 | 25. | 10280 | 408 | 170 | 2.60 |
| 27.7 | 0.0 | 25. | 11440 | 457 | 160 | 2.80 |

The invention has been described in detail with particular reference to preferred embodiments thereof, but it will be understood that variations and modifications can be effected within the spirit and scope of the invention.

What is claimed is:

1. A fermentative process for production of creatinine iminohydrolase from a creatinine iminohydrolase-producing aerobic soil microorganism comprising:
   A. in the first phase, inserting the microorganism in a production medium having a pH in the range of about 7 to about 8 to generate, under aerobic conditions, microorganisms in which creatinine iminohydrolase production has been induced, said production medium representing an aqueous nutrient medium which comprises:
      1) a carbon source comprising α-ketoglutaric acid,
      2) a nitrogen source comprising a source of ammonia, and
      3) trace nutrients, and
   B. after the first phase and when ammonia is substantially exhausted, incrementally adding a solution of creatinine at a rate of 0.5 to 3 grams of solution of creatinine per liter per hour,
   C. controlling the pH throughout the fermentation at about 7 to 8 by addition of an aqueous solution containing α-ketoglutaric acid, glucose, and inorganic salts, and
   D. extracting urease-free creatinine iminohydrolase from said medium in step B.

2. A fermentation process for production of creatinine iminohydrolase as defined in claim 1 wherein the carbon source in step A also comprises glucose.

3. A fermentation process for production of creatinine iminohydrolase as defined in claim 1 wherein the nitrogen source in step A comprises ammonium sulfate.

4. A fermentation process as in claim 3 wherein the ammonium sulfate is present in an amount of from 5 to 20 grams per liter.

5. A fermentation process as in claim 1 wherein the solution added in step B to control pH also comprises glucose.

6. A fermentation process as in claim 1 wherein the trace nutrients comprise inorganic salts.

7. The process of claim 1 wherein the carbon source in step A comprises 20 to 30 grams per liter α-ketoglutaric acid and 10 grams per liter glucose, and the nitrogen source contains only ammonium sulfate.

8. A fermentation process for production of urease-free creatinine iminohydrolase from *Flavobacterium filamentosum* comprising:
   A. in the first phase, inserting the microorganism in a production medium having a pH in the range of about 7 to about 8 to generate, under aerobic conditions, microorganisms in which creatinine iminohydrolase production has been induced, said production medium representing an aqueous nutrient medium which comprises:
      1) a carbon source comprising α-ketoglutaric acid,
      2) a nitrogen source comprising a source of ammonia, and
      3) trace nutrients, and
   B. after the first phase and when ammonia is substantially exhausted, incrementally adding creatinine at a rate of 0.5 to 3 grams creatinine per liter per hour,
   C. controlling the pH throughout the fermentation at about 7 to 8 by addition of an aqueous solution containing α-ketoglutaric acid, glucose, and inorganic salts, and
   D. extracting urease-free creatinine iminohydrolase from said medium in step B.

9. A fermentation process as in claim 8 wherein the creatinine feed in step B is from 0.5 to 3 grams per liter per hour for from 5 to 20 hours.

10. The fermentation process of claim 8 wherein the nutrient in step A contains trace elements.

11. The fermentation process of claim 10 wherein the trace elements comprise Mg, Fe, $Mn^2$, Na, Cl, $Mo^6$, $Ca^2$, and $Zn^2$.

12. An improved aqueous nutrient medium for growing under aerobic conditions a creatinine iminohydrolase-producing aerobic soil microorganism, said medium having a pH in the range of about 7 to about 8 and comprising:
 i) a carbon source comprising α-ketoglutaric acid, and
 ii) a nitrogen source consisting essentially of an ammonia source.

13. The medium of claim 12 wherein the nitrogen source is ammonium sulfate.

14. The medium of claim 12 wherein the carbon source also comprises glucose.

15. The medium of claim 12 wherein the medium also comprises trace nutrients.

16. The medium of claim 15 wherein the trace nutrients comprise water-soluble inorganic salts.

17. An improved nutrient medium for growing under aerobic conditions *Flavobacterium filamentosum*, said medium having a pH in the range of about 7 to 8 and comprising:
 i) a carbon source comprising α-ketoglutaric acid, and
 ii) a nitrogen source consisting essentially of an ammonia source.

18. The medium of claim 17 wherein the nitrogen source is ammonium sulfate.

* * * * *